United States Patent
Langer et al.

(10) Patent No.: US 9,101,695 B2
(45) Date of Patent: *Aug. 11, 2015

(54) METHODS AND COMPOSITIONS FOR THE TREATMENT OF OPEN AND CLOSED WOUND SPINAL CORD INJURIES

(71) Applicants: Children's Medical Center Corporation, Boston, MA (US); Massachusetts Institute of Technology, Cambridge, MA (US)

(72) Inventors: Robert S. Langer, Newton, MA (US); Rajiv Saigal, Philadelphia, PA (US); Yang Teng, Wellesley, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/496,742

(22) Filed: Sep. 25, 2014

(65) Prior Publication Data

US 2015/0030659 A1    Jan. 29, 2015

Related U.S. Application Data

(60) Continuation of application No. 14/177,888, filed on Feb. 11, 2014, now Pat. No. 8,858,966, which is a continuation of application No. 13/741,901, filed on Jan. 15, 2013, now Pat. No. 8,685,434, which is a (Continued)

(51) Int. Cl.
*A61L 31/06*   (2006.01)
*A61K 9/00*   (2006.01)

(Continued)

(52) U.S. Cl.
CPC . *A61L 31/06* (2013.01); *A61F 2/02* (2013.01); *A61K 9/0085* (2013.01); *A61L 27/26* (2013.01);

(Continued)

(58) Field of Classification Search
CPC .................................................. A61K 9/0085
See application file for complete search history.

(56) References Cited

U.S. PATENT DOCUMENTS

| | | | |
|---|---|---|---|
| 4,950,258 | A | 8/1990 | Kawai et al. |
| 4,955,893 | A | 9/1990 | Yannas et al. |

(Continued)

FOREIGN PATENT DOCUMENTS

| | | |
|---|---|---|
| EP | 1 084 720 B1 | 3/2005 |
| WO | WO9918892 | 4/1999 |

(Continued)

OTHER PUBLICATIONS

Borgens et al., Subcutaneous tri-block copolymer produces recovery from spinal cored injury, J. Neurosci. Res. 76:141-154, 2004.

(Continued)

*Primary Examiner* — Paul Dickinson
(74) *Attorney, Agent, or Firm* — Fish & Richardson P.C.

(57) ABSTRACT

Devices and methods for the treatment of open and closed wound spinal cord injuries are disclosed. For example, described herein are devices and methods for mitigating secondary injury to, and promoting recovery of, spinal cord primary injuries. More particularly, certain embodiments of the present invention are directed to polymeric mini-tubes that may be used for the treatment of spinal cord injuries. In addition, other embodiments are directed to polymeric "fill-in" bandages that may be used for the treatment of spinal cord injuries. For example, an erodible, or biodegradable, form of biocompatible polymer of the present invention is fabricated for surgical implantation into the site of the spinal cord injury.

18 Claims, 9 Drawing Sheets

Related U.S. Application Data division of application No. 11/789,538, filed on Apr. 25, 2007, now Pat. No. 8,377,463.

(60) Provisional application No. 60/794,986, filed on Apr. 25, 2006.

(51) Int. Cl.

| | |
|---|---|
| *A61F 2/02* | (2006.01) |
| *A61L 31/14* | (2006.01) |
| *A61L 27/26* | (2006.01) |
| *A61L 27/58* | (2006.01) |
| *A61L 31/16* | (2006.01) |

(52) U.S. Cl.
CPC .............. *A61L 27/58* (2013.01); *A61L 31/14* (2013.01); *A61L 31/148* (2013.01); *A61L 31/16* (2013.01); *A61F 2210/0004* (2013.01); *A61L 2300/412* (2013.01); *A61L 2430/38* (2013.01)

(56) References Cited

U.S. PATENT DOCUMENTS

| | | |
|---|---|---|
| 5,226,914 A | 7/1993 | Caplan et al. |
| 5,670,151 A | 9/1997 | Larrick et al. |
| 6,095,148 A | 8/2000 | Shastri et al. |
| 6,613,089 B1 | 9/2003 | Estes et al. |
| 6,696,575 B2 | 2/2004 | Schmidt et al. |
| 8,858,966 B2 | 10/2014 | Langer et al. |
| 2002/0137706 A1 | 9/2002 | Gregory et al. |
| 2003/0066987 A1 | 4/2003 | Schmidt et al. |
| 2003/0204197 A1 | 10/2003 | Onyekaba |
| 2005/0085790 A1 | 4/2005 | Guest et al. |
| 2005/0251267 A1 | 11/2005 | Winterbottom et al. |
| 2006/0002978 A1 | 1/2006 | Shea et al. |
| 2006/0036253 A1 | 2/2006 | Leroux et al. |
| 2006/0100647 A1 | 5/2006 | Doi et al. |
| 2007/0213701 A1 | 9/2007 | Kraft |
| 2007/0243228 A1 | 10/2007 | McKay |
| 2007/0259020 A1 | 11/2007 | Langer et al. |
| 2008/0183292 A1 | 7/2008 | Trieu |

FOREIGN PATENT DOCUMENTS

| | | |
|---|---|---|
| WO | WO02076288 | 10/2002 |
| WO | WO2007084609 | 7/2007 |
| WO | WO2007127790 | 11/2007 |

OTHER PUBLICATIONS

English translation of Office Action issued in Korean application No. 10-2008-7028672 issued on Jul. 10, 2013 (11 pages).
Examination Report issued in SG2011054061 on Apr. 28, 2014 (6 pages).
Gautier et al., Poly(alpha-hydroxyacids) for applicantion in the spinal cord: Resorbability and biocompatibility with adult rat Schwann cells and spinal cord, J. Biomed. Mater. Res. 4:642-654, Dec. 1998.
George et al., "Fabrication and biocompatibility of ploypyrrole implants suitable for neural prosthetics," Biomaterials, 26:3511-3519 (2005).
Harris, Spinal Deformity after Spinal Cord Injury, Paraplegia, 1969, 6(4), 232-238.
Hiraizumi et al., "Applicant of Polyvinyl Alcohol Hydrogel Membrane as Anti-adhesive Interposition After Spinal Surgery", Spine 21:2272-2277, 1995.
Huang and Huang, "Biomaterials and Strategies for Nerve Regeneration," Artificial Organs, 30(7):514-522 (2006).
International Search Report, International Application No. PCT/US2008/07226, 3 pages, Apr. 21, 2009.
Kotwal et al., "Electrical Stimulation Alters Protein Adsorption and Nerve Cell Interactions with Electrically Conducting Biomaterials", Biomaterials, vol. 22, No. 10, pp. 1055-1064, 2001.
Lavik, Erin Baker, "Functional Recovery Following Traumatic Spinal Cord Injury Mediated by a Novel Polymer Scaffold Seeded with Neural Stem Cells," Submitted to the Department of Materials Science and Engineering in partial fulfillment of the requirements for the Degree of Doctor of Science in Materials Science and Engineering, Massachusetts Institute of Technology (Jun. 2001).
Lee et al., "Three-Dimensional Cell Culture Matrices: State of the Art," Tissue Engineering: Part B, 14(1):61-86 (2008).
Liu et al., "A self-assembling peptide reduces glial scarring, attenuates post-traumatic inflammation and promotes neurological recovery following spinal cord injury," Acta Biomaterialia, 9:8075-8088 (2013).
Luo et al., Diffusive Oxidative Stress Following Acute Spinal Cord Injury in Guinea Pigs and its Inhibition by Polyethylene Glycol, Neurosci. Lett. 359:167-170, 2004.
Madigan et al., "Current tissue engineering and novel therapeutic approaches to axonal regeneration following spinal cord injury using polymer scaffolds," Respiratory Physiology & Neurobiology, 169:183-199 (2009).
Maquet et al., (Poly(D,L-lactide) foams modified by poly(ethylene oxide)-block-poly(D,L-lactide) copolymers and a-FGF: in vitro and in vivo evaluation for spinal cord regeneration, Biomaterials, 2001, 1137-1146.
Moore et al., "Multiple-channel scaffolds to promote spinal cord axon regeneration," Biomaterials 27, 419-429, 2006.
Novikova et al., "Biopolymers and Biodegradable Smart Implants for Tissue Regeneration After Spinal Cord Injury", Current Opinion in Neurology, vol. 16, No. 6, pp. 711-715, 2003.
Office Action issued in AU2008360388 on Apr. 14, 2014 (3 pages).
Office Action issued in AU2012227370 on Jan. 10, 2014 (3 pages).
Office Action issued in Canadian Patent Application No. 2,650,804 on Aug. 12, 2013 (3 pages).
Office Action issued in Chinese Patent Application No. 200880131305.9 on Mar. 5, 2013 (translation).
Office Action issued in CN 200780022752.6 on Aug. 14, 2013 (6 pages) (with translation).
Office Action issued in EP 07761270.3 on Jan. 20, 2014 (5 pages).
Office Action issued in JP2011-522037 on Oct. 25, 2013 (translation) (3 pages).
Office Action issued in SG201100824-0 on Dec. 26, 2013 (10 pages).
Office Action, Chinese Patent Application 200780022752.6, Mar. 15, 2013 (translation).
Office Action, Japanese Patent Application No. 2009-507940, Jul. 27, 2012.
Qudega et al., Axonal regeneration into Schwann cell grafts within resorbable poly(alpha-hydroxyacid) guidance channels in the adult rat spinal cord, Biomaterials, 2001, 22, 1125-1136.
Redmond et al., Proceedings of the National Academy of Science, vol. 104, No. 29, 12175-80, Jul. 17, 2007.
Schmidt and Leach, "Neural Tissue Engineering: Strategies for Repair and Regeneration," Annu. Rev. Biomed. Eng., 5:293-347 (2003).
Schmidt et al., "Stimulation of Neurite Outgrowth Using an Electrically Conducting Polymer", Proc. Natl. Acad. Sci. USA, vol. 94, No. 17, pp. 8948-8953, 1997.
Search Report and Written Opinion, Singapore Patent Application No. 201100824-0, 18 pages, Aug. 21, 2012.
Supplementary European Search Report; Publication issued; Jun. 6, 2012; EP07761270; 7 pages.
Teng et al., Functional recovery following traumatic spinal cord injury mediated by a unique polymer scaffold seeded with neural stem cells, Proceedings of the National Academy of Sciences, USA, 2002, 99, 3024-3029.
Translation of Office Action issued in KR10-2008-7028672 on May 1, 2014 (2 pages).
Tsai et al., "Matrix inclusion within synthetic hydrogel guidance channels improves specific supraspinal and local axonal regeneration after complete spinal cord transection", Biomaterials 27:519-533, 2006.
Tsai et al., "Synthetic Hydrogel Guidance Channels Facilitate Regeneration of Adult Rat Brainstem Motor Axons After Complete Spinal Cord Transection", Journal of Neurotrauma, vol. 21, No. 6, pp. 789-804, 2004.

(56) References Cited

OTHER PUBLICATIONS

Wang et al., "In vivo evaluation of a novel electrically conductive polypyrrole/poly(D,L-lactide) composite and polypyrrole-coated poly(D,L-lactide-co-glycolide) membranes," Journal of Biomedical Research Part A, 70 A(1): 28-38 (2004).
Wang et al., Evaluation of Biocompatibility of Polypyrrole In Vitro and In Vivo, J. Biomed Mater Res. A, vol. 68, No. 3, pp. 411-422, 2004.
Woerly et al., "Spinal Cord Repair with PHPMA Hydrogel Containing RGD Peptides (NeuroGelTM)", Biomaterials, vol. 22, Issue 10, pp. 1095-1111, 2001.
Written Opinion, International Application No. PCT/US2008/072226, 4 pages, Apr. 21, 2009.
Yang et al., Neurotrophin releasing single and multiple lumen nerve conduits, Journal of Controlled Release, 2006, 104, 433-446.
Zhong and Bellamkonda, "Biomaterials for the central nervous system," J. R. Soc. Interface, 5:957-975 (2008).
Office Action issued in CA2,650,804 on Jul. 7, 2014 (2 pages).
Office Action issued in JP2013-086578 on May 13, 2014 no translation (3 pages).
Office Action issued in KR-10-2013-7032762 on Jul. 18, 2014 with translation (6 pages).
Office Action issued in SG2011008240 on Jul. 18, 2014 (10 pages).
Office Action issued in CA2,733,252 on Aug. 1, 2014 (4 pages).
Office Action issued in Korean Patent Application No. 10-2008-7028672 on Sep. 3, 2014 with translation (5 pages).
Office Action issued in Indian Patent Application No. 5785/CHENP/2008 on Jan. 22, 2015 (2 pages).
Office Action issued in Korean Patent Application No. 10-2011-7005148 on Nov. 25, 2015 with translation (10 pages).
Office Action issued in CA2,650,804 on Apr. 13, 2015 (3 pages).
Office Action issued in KR10-2014-7024979 on Apr. 17, 2015 with English Translation (4 pages).
Reynolds, Francis M., "InVivo Therapeutics Corporation", Submitted to the Sloan School of Management in Partial Fulfillment of the Requirements for the Degree of Master in Business Administration in Conjunction with the Sloan Fellows Program in Innovation and Global Leadership, 2006 (100 pages).

A.

B.

C.

D.

METHODS AND COMPOSITIONS FOR THE TREATMENT OF OPEN AND CLOSED WOUND SPINAL CORD INJURIES

RELATED APPLICATION

Pursuant to 35 USC §120, this application is a continuation of prior U.S. application Ser. No. 14/177,888, filed Feb. 11, 2014, now U.S. Pat. No. 8,858,966, which is a continuation of prior U.S. application Ser. No. 13/741,901, filed Jan. 15, 2013, now U.S. Pat. No. 8,685,434, which in turn is a divisional application and claims the benefit of prior U.S. application Ser. No. 11/789,538, filed Apr. 25, 2007, now U.S. Pat. No. 8,377,463, which in turn claims the benefit of prior U.S. Provisional Application 60/794,986, filed Apr. 25, 2006. Each of these applications are incorporated by reference in its entirety.

BACKGROUND OF THE INVENTION

Many spinal cord injuries (SCIs) are a result of the spinal cord being compressed, not cut. Insult to the spinal cord often results in vertebrae, nerve and blood vessel damage. Bleeding, fluid accumulation, and swelling can occur inside the spinal cord or outside the spinal cord but within the vertebral canal. The pressure from the surrounding bone and meninges structure can further damage the spinal cord. Moreover, edema of the cord itself can additionally accelerate secondary tissue loss. There is considerable evidence that the primary mechanical injury initiates a cascade of secondary injury mechanisms including excessive excitatory neurotransmitter accumulation; edema formation; electrolyte shifts, including increased intracellular calcium; free radical production, especially oxidant-free radicals; and eicosanoid production. Therefore, SCIs can be viewed as a two-step process. The primary injury is mechanical, resulting from impact, compression or some other insult to the spinal column. The secondary injury is cellular and biochemical, wherein cellular/molecular reactions cause tissue destruction. By interrupting this second process and diffusing any compression resulting from the primary mechanical lesion, as well as any cord edema, healing is expedited.

As discussed above, spinal cord injury involves not only initial tissue injury, but also devastating secondary injuries. These pathological events, caused by excitotoxicity, free-radical formation and lack of neurotrophic support, include glial scarring, myelin-related axonal growth inhibition, demyelination, secondary cell death such as apoptosis. For example, oligodendrocyte death continues for weeks after many SCIs. An environment antagonistic to axonal regeneration is subsequently formed. In addition to damaged regeneration pathways, reflexia hyperexcitability and muscle spasticity, there are further complications of respiratory and bladder dysfunction, for example. Over time, muscle mass is lost as a result of loss of innervations and non-use. The end result of these spinal cord insults invariably is lost function, the extent of which is determined by the severity of the spinal cord primary lesion as well as by secondary injuries. Even in the case of incomplete motor function loss, common problems include posture, reduced walking speed, abnormal balance and gait, and lack of sufficient weight-bearing.

Surgical decompression of the spinal cord is often used to relieve any pressure from surrounding bone (by removing fractured or dislocated vertebrae or disks). However, the timing of surgical decompression has been a controversial topic. While rat studies have shown early decompression to reduce secondary injury, the results in human clinical trials have been less than consistent. It has been difficult to determine a time window for the effective application of surgical decompression intervention in the clinical setting. Furthermore, there are no technologies which can be used to effectively control the increase in intra-parenchyma pressure resulting from the primary SCI. The absence of such a technology renders surgical decompression surgery, in many cases, ineffective. The removal of bone and soft tissue structures do not address the underlying problem of secondary intrinsic pressure at the SCI site. Therefore, there exists a need to provide alternative devices and methods to impede the process that drive secondary injury at the primary spinal cord injury site. These alternative methods can be used to complement decompression surgical protocols.

There has been scant, if any, therapeutic attention given to the intrinsic nature of the injured/compressed spinal cord (i.e. the injured/compressed cord itself). As mentioned above, decompression surgery is directed to the extrinsic nature of the injury (i.e. removal of bone or fluid surrounding, and causing, the injury) in hopes of alleviating consequences of intra-tissue pressure build-up. Secondary injury will often impede the nerve regeneration and/or nerve regrowth process. Consequently, there exists a need for devices and methods that alleviate the primary spinal cord injury from, for example, secondary tissue destruction, edema formation, and an influx of inflammatory factors.

Furthermore, it is well known that penetrating spinal cord injuries (SCIs) are the most deadly neurotrauma encountered by people. Reports on combat related open wound SCIs during the Vietnam war indicate that this type of injury leads to close to 100% lethality. While there have been advances in the protective ability of bullet-proof vests, the neck region of persons wearing many of today's vests is often vulnerable to many high velocity weapons. More than 90% of SCIs are initially diagnosed as "incomplete," wherein the injury does not result in complete severing of the spinal cord. Technology which can protect the spared tissue and promote endogenous healing and repair will mitigate functional deficits resulting from both penetrating and contusion traumatic SCIs.

BRIEF SUMMARY OF THE INVENTION

Certain embodiments of the present invention are directed to biocompatible polymeric materials which can be fabricated into "mini-tubes," or "tubular articles." These mini-tubes can be used to treat any localized SCI. In one embodiment, the mini-tube is inserted into the epicenter of the injury, wherein the hollow tube runs through the injury site. See FIG. 1. The mini-tube can be inserted through a surgical incision made rostral or caudal to the lesion to be treated. The mini-tube creates a new interface within the compressed spinal cord parenchyma. This new interface relieves the site of pressure and protects tissue that has been spared from injury. Pressure resulting from the compression force exerted on the cord is alleviated by (1) diffusing or redirecting the force down the surface of the mini-tube and away from the initial compressed site, and (2) absorbing the compression energy into the biocompatible material of the mini-tube. See FIG. 1. Furthermore, by providing a structure between the injured site and surrounding tissue (the new interface), inflammation may be mitigated in the adjacent area where functionally relevant residual cord tissue can be spared.

In another embodiment, the present invention relates to biocompatible polymers fabricated into hollow mini-tubes, or tubular articles, having an inner surface, an outer surface and two opposing ends. The mini-tubes may be fabricated into any geometrical shape and size. For example, the size and the shape of the mini-tube may be varied in order to deliver more effective relief. A thin, elongated cylinder is one possible configuration, but other shapes, such as elongated rectangular tubes, spheres, helical structures, and others are possible. Additional alterations in configuration, such as the number, orientation, and shape of the mini-tubes may be varied in order to deliver more effective relief. For instance, the mini-tubes may be rectangular, or any other useful shape, and may be distributed along and/or around epicenter of the spinal cord injury. The size will vary accordingly with the spinal cord lesion to be treated. The mini-tube can be smaller than, the same size as, or longer than the lesion to be treated. In preferred embodiment, the mini-tube will be longer than the length of the injured site. In another preferred embodiment, the length of the mini-tube to be surgically implanted will be approximately between 1.2 and 3 times the length of the injured site or lesion running lengthwise along the spinal cord. In yet another preferred embodiment, the mini-tube will extend beyond the caudal and rostral sides of the injured site at a distance of approximately ¼ the length of the injured site. In a preferred embodiment the mini-tube will extend equally beyond the caudal and rostral sides of the injured site.

The diameter of the mini-tube (outer surface to outer surface; or "outside diameter") can range from 0.1 microns to 10 millimeters. In a preferred embodiment, the overall diameter of the mini-tube (outer surface to outer surface) is between about 5 and 200 microns. In other embodiments the diameter of the mini-tube (outer surface to outer surface) is between about 20 and 200 microns, between about 50 and 175 microns, between about 100 and 200 microns, and between about 150 and 300 microns. In another embodiment, the diameter of the mini-tube (outer surface to outer surface) is between about 0.5 millimeters and 20 millimeters. In other embodiments, the diameter of the mini-tube (outer surface to outer surface) is between about 1 millimeter and 10 millimeters, between about 1 millimeter and 5 millimeters, and between about 1 millimeter and 3 millimeters.

The diameter of the mini-tube (inner surface to inner surface; or the "lumen diameter") can also range from microns to millimeters. In a preferred embodiment, the diameter of the mini-tube (lumen diameter) is between about 5 and 200 microns. In other embodiments the diameter of the mini-tube (lumen) is between about 20 and 200 microns, between about 50 and 175 microns, between about 100 and 200 microns, and between about 150 and 300 microns. In another embodiment, the diameter of the mini-tube (lumen) is between about 0.5 millimeters and 15 millimeters. In other embodiments, the diameter of the mini-tube (lumen) is between about 1 millimeter and 10 millimeters, between about 1 millimeter and 5 millimeters, and between about 1 millimeter and 3 millimeters.

In another embodiment of the present invention, formable, moldable, biocompatible polymeric materials are disclosed herein. Advantageously, the polymeric material may be fabricated as a putty. By "putty" it is meant that the material has a dough-like consistency that is formable or moldable. These materials are sufficiently and readily moldable and can be formed into flexible three-dimensional structures or shapes complementary to a target site to be treated.

In yet another embodiment, the biocompatible polymeric materials of the present invention can be fabricated into readily formable or moldable bandages, or neuropatches. In one embodiment, a SCI is localized and the bandage or neuropatch is hand-formed to complement the injured site (for example, a hemi-sected spinal cord). The hand formed bandage is then implanted into the epicenter of the injury, wherein the bandage fills in the injury site. The implanted bandage bridges any gap formed by the spinal cord lesion and functions as an artificial pathway, nurturing regrowing neurons, reorganizing neurites and helping to form functional synapses. This new bandage interface allows for interactions between endogenous neural cells (including neural stem cells, if incorporated onto the bandage) and the inhibitory molecule-free polymer implant environment to promote cell survival. Furthermore, by providing a structure between the injured site and surrounding tissue (the new interface), inflammation may be mitigated in the adjacent area where functionally relevant residual cord tissue can be spared.

In another embodiment, the present invention relates to biocompatible polymeric bandages, which can be readily fabricated/formed into any shape and size, comprising a single polymeric scaffold having an inner surface and an outer surface. See example 15. The formed bandages may be fabricated into any geometrical shape and size. For example, the size and the shape of the bandage may be varied in order to deliver more effective relief. A thin, elongated bandage is one possible configuration, but other shapes, such as elongated rectangular bandages, spheres, helical structures, and others are possible. Additional alterations in configuration, such as the number, orientation, and shape of the bandages may be varied in order to deliver more effective relief. For instance, the bandages may be rectangular, or any other useful shape, and may be distributed within and/or around epicenter of the spinal cord injury. In addition, the bandage may have a textured surface including a plurality of pores and/or microgrooves on its inner and/or outer surface. In one embodiment, the pores have diameters between about 0.5 µm to 4 µm and depths of at least 0.5 µm. The microgrooves may have widths of between about 0.5 µm and 4 µm and depths of at least 0.5 µm. The sizes of the bandage, and the sizes and diameters of its pores and microgrooves, will vary accordingly with the spinal cord lesion to be treated. The pores and/or microgrooves on the inner and/or outer surface may be seeded with one or more medicinal agents, for example human neuronal stem cells to provide cellular replacement and trophic support. In preferred embodiment, the bandage will act as a filler (i.e. fill the lesion) after implantation of the bandage within the lesioned area of the spinal cord, for example. In one embodiment, the bandage inner surface is flush with the lesioned spinal cord, i.e. contacts the lesion, when it is implanted.

Biocompatible polymers for the fabrication of the herein described mini-tubes and formable bandage or neuropatch articles are well-known in the art. In a preferred embodiment, the biocompatible polymers are biodegradable (for example, PLGA). As used herein, biodegradable and erodible are used interchangeably. Examples of biocompatible polymers that are biodegradable include, but are not limited to, biodegradable hydrophilic polymers such as polysaccharides, proteinaceous polymers, soluble derivatives of polysaccharides, soluble derivatives of proteinaceous polymers, polypeptides, polyesters, polyorthoesters, and the like. The polysaccharides may be poly-1,4-glucans, e.g., starch glycogen, amylose and amylopectin, and the like. Preferably, biodegradable hydrophilic polymers are water-soluble derivatives of poly-1,4-glucan, including hydrolyzed amylopectin, hydroxyalkyl derivatives of hydrolyzed amylopectin such as hydroxyethyl starch (HES), hydroxyethyl amylase, dialdehyde starch, and the like. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-leucine, L-valine, L-tyrosine, and the like.

Definitions or further description of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W. H. Freeman and Company, both of which are hereby incorporated by reference.

The aforementioned biodegradable hydrophilic polymers are particularly suited for the methods and compositions of the present invention by reason of their characteristically low human toxicity and virtually complete biodegradability. Of course, it will be understood that the particular polymer utilized is not critical and a variety of biodegradable hydrophilic polymers may be utilized as a consequence of the novel processing methods of the invention.

Electrical signals in the form of action potentials are the means of signaling for billions of cells in the central nervous system. Numerous studies have shown that this electrical activity is not only a means of communication, but also necessary for the normal development of the nervous system and refinement of functional neural circuits. In the case of spinal cord injury, cell-to-cell communication may be interrupted and the mechanisms of normal neurological development imply that electrical activity should be part of the restoration of functional connections. Such activity is important for the survival of existing cells and the incorporation of any transplanted cells (such as neural stem cells) into working circuits. In an embodiment of the present invention, single and double layer scaffolds and minitubes are fabricated from synthetic biomaterials and are capable of conducting electricity and naturally eroding inside the body. In an exemplary embodiment, the single scaffold, double scaffold, or minitube comprises a biocompatible polymer capable of conducting electricity is a polypyrrole polymer. Polyaniline, polyacetyline, poly-p-phenylene, poly-p-phenylene-vinylene, polythiophene, and hemosin are examples of other biocompatible polymers that are capable of conducting electricity and may be used in conjunction with the present invention. Other erodible, conducting polymers are well known (for example, see Zelikin et al., Erodible Conducting Polymers for Potential Biomedical Applications, Angew. Chem. Int. Ed. Engl., 2002, 41(1):141-144). Any of the foregoing electrical conducting polymers can be applied or coated onto a malleable or moldable article. The coated article can be also be used as a bandage, or neuropatch, as described herein.

In a preferred embodiment the biodegradable and/or bioabsorbable polymer contains a monomer selected from the group consisting of a glycolide, lactide, dioxanone, caprolactone, trimethylene carbonate, ethylene glycol and lysine. By the terminology "contains a monomer" is intended a polymer which is produced from the specified monomer(s) or contains the specified monomeric unit(s). The polymer can be a homopolymer, random or block co-polymer or hetero-polymer containing any combination of these monomers. The material can be a random copolymer, block copolymer or blend of homopolymers, copolymers, and/or heteropolymers that contains these monomers.

In one embodiment, the biodegradable and/or bioabsorbable polymer contains bioabsorbable and biodegradable linear aliphatic polyesters such as polyglycolide (PGA) and its random copolymer poly(glycolide-co-lactide) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidney. These polymers are different from cellulose based materials, which cannot be absorbed by the body.

The molecular weight (MW) of the polymers used in the formable articles of the presently described invention can vary according to the polymers used and the degradation rate desired to be achieved. In one embodiment, the average MW of the polymers in the fabricated bandage is between about 1,000 and about 50,000. In another embodiment, the average MW of the polymers in the fabricated bandage is between about 2,000 and 30,000. In yet another embodiment, the average MW is between about 20,000 and 50,000 for PLGA and between about 1,000 and 3,000 for polylysine.

The herein described mini-tubes and formable articles may be incorporated with any number of medically useful substances. In a preferred embodiment, the inner and/or outer surfaces of the mini-tube is seeded with stem cells; for example, mesenchymal and/or neuronal stem cells, wherein the cells are deposited onto the inner (lumen in the case of the mini-tubes) and/or outer surface(s). See FIG. 3. The incorporation of stem cells provide for trophic support and/or cellular replacement at the site of injury.

In another embodiment, the foregoing described polymeric articles are used in methods for providing controlled tissue healing. These methods comprise, for example, implanting into a target compression injury site in an animal, a system for controlled tissue healing, the system comprising a biodegradable and/or bioabsorbable polymeric hollow tube. The target injury site may be any injury that is susceptible to secondary tissue injury, including but not limited to: glial scarring, myelin inhibition, demyelination, cell death, lack of neurotrophic support, ischemia, free-radical formation, and excitotoxicity. In one embodiment, the injury to be treated is a spinal cord injury, wherein the spinal cord is compressed. The herein described methods may be used in conjunction with decompression surgery; for example, concomitant with decompression surgery, prior to decompression surgery, or subsequent to decompression surgery.

In another embodiment, the foregoing described polymeric articles are used in methods for treating a compression spinal cord injury comprising implanting into a target compression injury site in an animal a biodegradable and/or bioabsorbable polymeric hollow tube. The spinal cord injury may be susceptible to secondary tissue injury, including but not limited to: glial scarring, myelin inhibition, demyelination, cell death, lack of neurotrophic support, ischemia, free-radical formation, and excitotoxicity. The herein described methods may be used in conjunction with decompression surgery; for example, concomitant with decompression surgery, prior to decompression surgery, or subsequent to decompression surgery.

GLOSSARY OF TERMS

Figure 1:
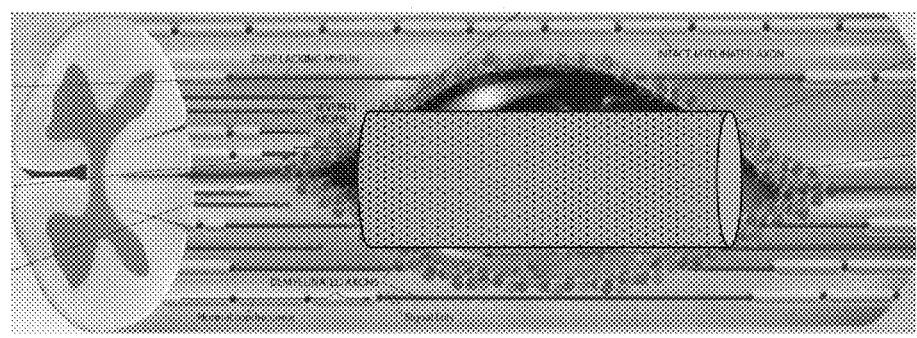
FIG. 1. Two schematic representations (A and B) of the polypyrrole scaffold inserted around the center of the lesion area in order to protect surrounding tissues.
Figure 1:
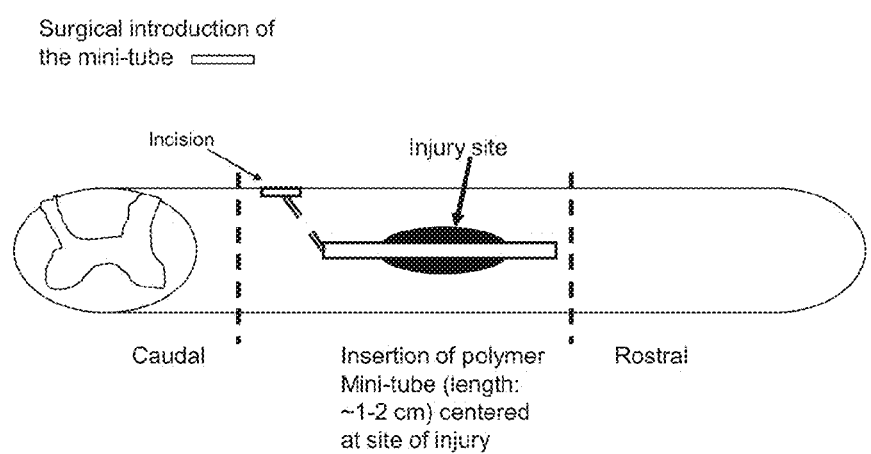

By the term biodegradable is intended a material which is broken down (usually gradually) by the body of an animal, e.g. a mammal, after implantation.

By the term bioabsorbable is intended a material which is absorbed or resorbed by the body of an animal, e.g. a mammal, after implantation, such that the material eventually becomes essentially non-detectable at the site of implantation.

By the terminology "biodegradable and/or bioabsorbable article or minitube" is intended any material which is biocompatible, as well as biodegradable and/or bioabsorbable, and capable of being formed into tubes, as described more fully herein. The material is also capable of being formed into articles which is suitable for implantation into an animal and capable of being biodegraded and/or bioabsorbed by the animal.

The biodegradable and/or bioabsorbable articles of the present invention are preferably biodegradable and bioabsorbable polymers. Examples of suitable polymers can be found in Bezwada, Rao S. et al. (1997) Poly(p-Dioxanone) and its copolymers, in Handbook of Biodegradable Polymers, A. J. Domb, J. Kost and D. M. Wiseman, editors, Hardwood Academic Publishers, The Netherlands, pp. 29-61, the disclosure of which is incorporated herein by reference in its entirety.

"Mini-tubes" and "tubular articles" are used interchangeably in the present description.

"Moldable" and "formable" are used interchangeably in the present description.

DETAILED DESCRIPTION OF THE INVENTION

Described herein are devices and methods for mitigating secondary injury to, and promoting recovery of, spinal cord primary injuries. More particularly, certain embodiments of the present invention are directed to polymeric mini-tubes that may be used for the treatment of spinal cord injuries. In addition, other embodiments are directed to polymeric "fill-in" bandages that may be used for the treatment of spinal cord injuries. For example, an erodible, or biodegradable, form of biocompatible polymer of the present invention is fabricated for surgical implantation into the site of the spinal cord injury.

Certain embodiments of the present invention are directed to biocompatible polymeric materials which can be fabricated into "mini-tubes." These mini-tubes can be used to treat the SCI once it has been localized. In one embodiment, the mini-tube is inserted into the epicenter of the injury, wherein the hollow tube runs through the injury site. See FIG. 1. The mini-tube creates a new interface within the compressed spinal cord parenchyma. This new interface relieves the site of pressure and protects tissue that has been spared from injury. Pressure resulting from the compression force exerted on the cord is alleviated by (1) diffusing or redirecting the force down the surface of the mini-tube and away from the initial compressed site, and (2) absorbing the compression energy into the biocompatible material of the mini-tube. See FIG. 1. Furthermore, by providing a structure between the injured site and surrounding tissue (the new interface), inflammation may be mitigated in the adjacent area where functionally relevant residual cord tissue can be spared.

An erodible, or biodegradable, form of biocompatible polymer of the present invention is fabricated into a mini-tube for surgical implantation into the site of the spinal cord injury. Surgical implantation results in a target area, for example a necrotic section of the spinal cord, that is encapsulated by the polymer. In one embodiment, the surgery results in complete encapsulation of the target area or only the central necrotic area. See FIG. 1. Encapsulation of the central necrotic area minimizes secondary injury by inhibiting cell-cell signaling with inflammatory cytokines. Shunting the fluid-filled cyst reduces pressure buildup within the cord and decreases injury to neurons. Bridging the gap formed by the cyst allows a pathway for regrowing neurons to reach the caudal side and form functional synapses.

In a preferred embodiment of the present invention, the biocompatible polymer is an electrically conductive material. This material allows conduction of endogenous electrical activity from surviving neurons, thereby promoting cell survival. Any such material should be bioresorbable in situ, such that it naturally erodes once its function has been performed. Finally, a three-dimensional scaffold creates a substrate by which cells can be grown in vitro and then implanted in vivo. A hollow cylindrical scaffold (mini-tube) made of polypyrrole (PPy), for example, meets all of these design requirements. A schematic of the design in situ is shown in FIG. 1. In an exemplary embodiment, the biocompatible polymer capable of conducting electricity is a polypyrrole polymer. Polyaniline, polyacetyline, poly-p-phenylene, poly-p-phenylene-vinylene, polythiophene, and hemosin are examples of other biocompatible polymers that are capable of conducting electricity and may be used in conjunction with the present invention. Other erodible, conducting polymers are well known (for example, see Zelikin et al., Erodible Conducting Polymers for Potential Biomedical Applications, Angew. Chem. Int. Ed. Engl., 2002, 41(1):141-144).

The polymeric mini-tubes of the present invention are not limited to electrical conducting polymers, such as PPy. Polymeric minitubes of the present invention may comprise one or more monomers selected from the group consisting of a glycolide, lactide, dioxanone, caprolactone, trimethylene carbonate, ethylene glycol and lysine, for example. Furthermore, it is possible for the polymeric bandages to comprise one or more biodegradable and/or bioabsorbable linear aliphatic polyesters, copolymer poly(glycolide-co-lactide), and/or material derived from biological tissue. Material derived from biological tissue can be, but is not limited to, neuronal and/or mesenchymal stem cells which can be used as medicinal agents.

Figure 3:
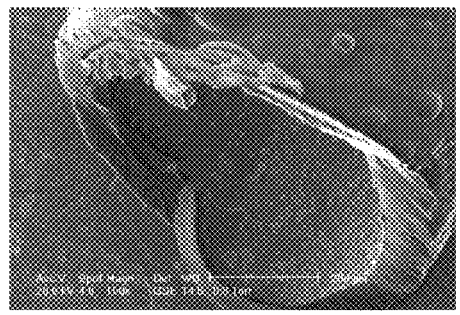
FIG. 3. SEM images of microfabricated PPy tubes. A. Murine neural stem cells seeded inside of a 600 µm inner diameter tube (150×). B. High-magnification (350×) view of 25 µm inner diameter tube. Rough surface texture is a result of low electrodeposition temperature (4° C.). C. Lower magnification (150×) view of a 25 µm inner diameter tube created with a smooth surface texture by electrodeposition at 24° C. D. Higher magnification (500×) view of same tube as in C.
Figure 3:
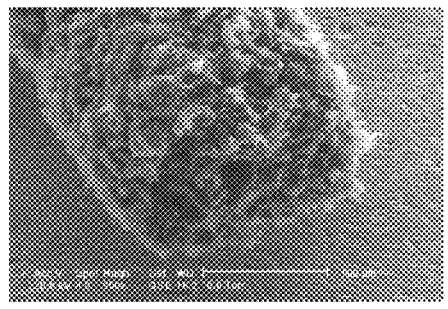
Figure 3:
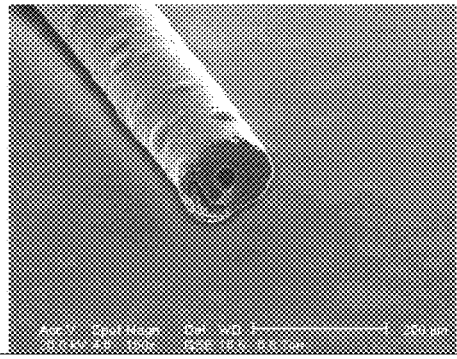
Figure 3:
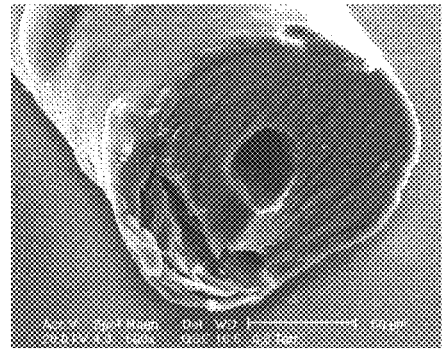

As described in further detail below, a biodegradable and/or bioabsorbable polymeric tubular article of the present invention can be formed by electrodeposition of an electrical conducting polymer onto a template conductive wire, wherein the polymer is released from the wire by applying a reverse potential to the template conductive wire in a saline solution. The polymeric minitubes of the present invention are not limited to electrical conducting polymers, such as PPy. Polymeric minitubes of the present invention may comprise one or more monomers selected from the group consisting of a glycolide, lactide, dioxanone, caprolactone, trimethylene carbonate, ethylene glycol and lysine, for example. Furthermore, it is possible for the polymeric minitubes to comprise one or more biodegradable and/or bioabsorbable linear aliphatic polyesters, copolymer poly(glycolide-co-lactide), and/or material derived from biological tissue. Material derived from biological tissue can be, but is not limited to, neuronal and/or mesenchymal stem cells which can be used as medicinal agents. See FIG. 3, for example.

Figure 2:
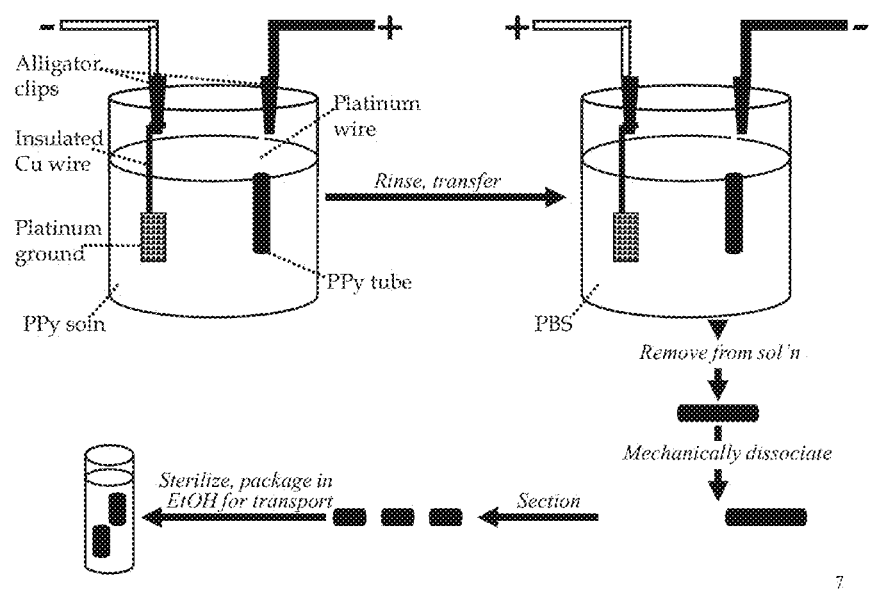
FIG. 2. Electrodeposition of erodible PPy to form mini-tube scaffolds.

An example of a type of method used to fabricate the mini-tube polymers described herein is shown in FIG. 2. The pattern of the conductive template for electrodeposition of polypyrrole (PPy), for example, controls the shape of the PPy scaffold that is created. By controlling the template, the polymer scaffold can be manufactured in different shapes and sizes, ranging from thin lines to rectangular planar implants, for example. See Example 5. Tube-like PPy scaffolds can be produced by plating the PPy onto a conductive wire. For scaffold removal from the template, a reverse potential is applied to the template in a saline solution. When applied for sufficient time and strength, the scaffold slides off of the wire mold with a slight pull. See Example 1. This method relieves the manufacturer of having to use harsh organics to etch the inner wire template, thereby resulting in polymeric devices that are ill-suited for use in vivo.

As described above, the mini-tubes may be fabricated into any geometrical shape and size. For example, the size and the shape of the mini-tube may be varied in order to deliver more effective relief. A thin, elongated cylinder is one possible configuration, but other shapes, such as elongated rectangular tubes, spheres, helical structures, and others are possible. Additional alterations in configuration, such as the number, orientation, and shape of the mini-tubes may be varied in order to deliver more effective relief. For instance, the mini-tubes may be rectangular, or any other useful shape, and may be distributed along and/or around epicenter of the spinal cord injury. The size (length and diameter) will vary accordingly with the spinal cord lesion to be treated. For example a cord lesion that is 10 microns in length (running along the length of the spinal cord) and 3 microns deep, may require a polymeric mini-tube of 15 microns in length and having an overall diameter of 2.5 microns. The polymeric mini-tube is surgically inserted through the lesion such that the central section of the lesion is encapsulated by the tube. In this example, the tube will extend approximately 2.5 microns beyond each of the caudal and rostral ends of the target lesioned area. The polymeric tubular articles of the present invention are preferred to have overall diameters of between about 0.1 microns and 10 millimeters. More preferred are articles having overall diameters of between about 50 and 175 microns. However, any size, diameter, length can be fabricated according the herein described methods in order to accommodate any lesion of the spinal cord.

The biocompatible and biodegradable polymeric mini-tubes of the present invention can contain pharmaceutically or biologically active substances such as, for example, anti-inflammatories, growth factors, and stem cells.

In another embodiment, the present invention is directed to polymeric "fill-in" bandages that may be used for the treatment of spinal cord injuries. For example, an erodible, or biodegradable, form of biocompatible polymer of the present invention is fabricated for surgical implantation into the site of the spinal cord injury. The implantation can be accomplished immediately after molding the bandage to conform to the injured site. The target area, for example a necrotic section of the spinal cord, may be encapsulated by the polymer, or alternatively, filled in with the formed polymer. The implantation may result in complete encapsulation of the target area or only the central necrotic area; or may result in a previously open lesioned area being filled in with the formed polymer. Encapsulation of the central necrotic area minimizes secondary injury by inhibiting cell-cell signaling with inflammatory cytokines. Bridging the gap formed by the lesion allows a pathway for regrowing neurons to reach the caudal side and the formation of functional synapses.

Optionally, an electrically conductive formable and biocompatible polymeric material may be used to allow conduction of endogenous electrical activity from surviving neurons, thereby promoting cell survival. Any such material should be bioresorbable in situ, such that it naturally erodes once its function has been performed. Finally, a three-dimensional scaffold creates a substrate by which cells can be grown in vitro and then transplanted in vivo. A bandage scaffold made of polypyrrole (PPy), for example, meets all of these design requirements. A schematic of the design in situ is shown in FIG. 1.

The polymeric bandages of the present invention are not limited to electrical conducting polymers, such as PPy. Polymeric bandages of the present invention may comprise one or more monomers selected from the group consisting of a glycolide, lactide, dioxanone, caprolactone, trimethylene carbonate, ethylene glycol and lysine, for example. Furthermore, it is possible for the polymeric bandages to comprise one or more biodegradable and/or bioabsorbable linear aliphatic polyesters, copolymer poly(glycolide-co-lactide), and/or material derived from biological tissue. Material derived from biological tissue can be, but is not limited to, neuronal and/or mesenchymal stem cells which can be used as medicinal agents.

The biocompatible and biodegradable polymeric bandages of the present invention may contain pharmaceutically or biologically active substances such as, for example, anti-inflammatories, growth factors, and stem cells. As described above, the polymer bandages may be fabricated into structures wherein the outer surface is an outer scaffold having long, axially oriented pores for axonal guidance and/or radial pores to allow fluid transport and inhibit ingrowth of scar tissue. See Example 7, below. The inner surface, or inner scaffold, may be porous and seeded with one or more medicinal agents, for example human neuronal stem cells for cellular replacement and trophic support. Therefore, in this particular embodiment, the fabricated and formed bandage comprises two scaffolds (a double scaffold) and simulates the architecture of a healthy spinal cord through an implant consisting of a polymer scaffold, perhaps seeded with neuronal stem cells. The inner scaffold emulates the gray matter; the outer portion emulates the white matter. The bandage can be readily designed to be tailored to fit into a variety of cavities.

In another embodiment, the present invention relates to biocompatible polymeric bandages, which can be readily fabricated/formed into any shape and size, comprising a single polymeric scaffold having an inner surface and an outer surface, wherein the formed bandages may be fabricated into any geometrical shape and size. This single polymeric scaffold may comprise pores (for example, on the surface making contact with the lesion) for incorporating medicinal agents and/or depositing neural stem cells. This porous single scaffold is fabricated as described in Example 15.

In another embodiment, the present invention relates to a medical article suitable for implanting within a patient's spinal cord. The article comprises a moldable biocompatible material comprising a 50:50 blend of (1) poly(lactic-co-glycolic acid) and (2) a block copolymer of poly(lactic-co-glycolic acid)-polylysine. The (1) poly(lactic-co-glycolic acid) is 75% poly(lactic-co-glycolic acid) and wherein the average molecular weight is Mn ~40,000. The (2) block copolymer of poly(lactic-co-glycolic acid)-polylysine is 25% poly(lactic-co-glycolic acid)-polylysine copolymer and wherein the average molecular weight of the poly(lactic-co-glycolic acid) block is Mn ~30,000 and the average molecular weight of the polylysine block is Mn ~2,000. In an alternative embodiment, the article comprises a single block of poly(lactic-co-glycolic acid). It is preferred that any of the foregoing articles have a degradation rate of about between about 30 and 60 days; however, the rate can be altered to provide a desired level of efficacy of treatment. The article may further comprise stem cells in association with any of the polymeric material. For example, the stem cells may be seeded onto the polymer or, more specifically, seeded within pores on the surface of the polymer. Any stem cell type may be used. It is preferable, for the treatment of spinal cord injury, that the stem cells be selected from neuronal stem cells and/or mesenchymal stem cells.

In yet another embodiment, the article comprises a single scaffold of an electrically conducting polymer, such as polypyrrole. It is preferred that any of the foregoing articles have a degradation rate of about between about 30 and 60 days; however, the rate can be altered to provide a desired level of efficacy of treatment. The article may further comprise stem cells in association with any of the polymeric material. For example, the stem cells may be seeded onto the polymer or, more specifically, seeded within pores on the surface of the polymer. Any stem cell type may be used. It is preferable, for the treatment of spinal cord injury, that the stem cells be selected from neuronal stem cells and/or mesenchymal stem cells.

In another embodiment of the present invention, a method is disclosed for treating an open wound spinal cord injury, comprising (a) molding a biocompatible material comprising a 50:50 blend of (1) poly(lactic-co-glycolic acid) and (2) a block copolymer of poly(lactic-co-glycolic acid)-polylysine to conform to a lesioned area of the spinal cord injury; and (b) filling in the lesioned area with the biocompatible material. The (1) poly(lactic-co-glycolic acid) is 75% poly(lactic-co-glycolic acid) and wherein the average molecular weight is Mn ~40,000. The (2) block copolymer of poly(lactic-co-glycolic acid)-polylysine is 25% poly(lactic-co-glycolic acid)-polylysine copolymer and wherein the average molecular weight of the poly(lactic-co-glycolic acid) block is Mn ~30,000 and the average molecular weight of the polylysine block is Mn ~2,000. It is preferred that the material has a degradation rate of about between about 30 and 60 days; however, the rate can be altered to provide a desired level of efficacy of treatment. The material may further comprise stem cells in association with any of the polymeric material. For example, the stem cells may be seeded onto the polymer or, more specifically, seeded within pores on the surface of the polymer. Any stem cell type may be used. It is preferable, for the treatment of spinal cord injury, that the stem cells be selected from neuronal stem cells and/or mesenchymal stem cells.

In yet another embodiment of the present invention, a method is disclosed for treating an open wound spinal cord injury, comprising double scaffold of polypyrrole to conform to a lesioned area of the spinal cord injury; and (b) filling in the lesioned area with the biocompatible polypyrrole material. The inner surface, or inner scaffold, may be porous and seeded with one or more medicinal agents, for example human neuronal stem cells for cellular replacement and/or trophic support. Therefore, in this particular embodiment, the fabricated and formed bandage comprises two scaffolds and simulates the architecture of a healthy spinal cord through an implant consisting of a polymer scaffold, perhaps seeded with neuronal stem cells. The inner scaffold emulates the gray matter; the outer scaffold (the second scaffold) emulates the white matter by having, for example, long, axially oriented pores for axonal guidance and radial porosity to allow fluid transport and inhibiting ingrowth of scar tissue. The bandage can be readily designed to be tailored to fit into a variety of cavities.

It is preferred that the polypyrrole has a degradation rate of about between about 30 and 60 days; however, the rate can be altered to provide a desired level of efficacy of treatment. The material may further comprise stem cells in association with any of the polymeric material. For example, the stem cells may be seeded onto the polymer or, more specifically, seeded within pores on the surface of the polymer. Any stem cell type may be used. It is preferable, for the treatment of spinal cord injury, that the stem cells be selected from neuronal stem cells and/or mesenchymal stem cells.

In another embodiment of the present invention, a kit for surgically treating spinal cord injuries is described. The kit may include any combination of the components, devices, and polymeric articles, discussed above, in one or more containers, including but not limited to: one or more pre-cut polymeric bandage scaffolds and/or mini-tube scaffolds, one or more artificial dura, a trimming tool, an alignment tool, drapes, and instructions for using the kit and components therein. The components of the kit may be packaged in a sterile manner as known in the relevant art.

EXAMPLES

The following non-limiting examples have been carried out to illustrate preferred embodiments of the invention.

Example 1

Polypyrrole Mini-Tube Fabrication (I)

Polypyrrole tube scaffolds are created by electrodeposition of erodible PPy at 100 µA for 30 minutes onto 250 µm diameter platinum wire. See FIG. 2. This is followed by reverse plating at 3 V for 5 minutes, allowing for the removal of the scaffold. See FIGS. 3(C and D).

Example 2

PPy Mini-Tubes Prevent Post-Primary Injury Cavity Formation in the Lesioned Spinal Cord (n=13, SCI and Control Rats, Respectively)

MRI images of post-injury cavity development, studied two months post injury, show large cavity formation in the control spinal cord (wherein injured cord was not treated with surgically implanted mini-tube), as compared to the PPy-treated spinal cord. See FIG. 4.

Example 3

Figure 4:
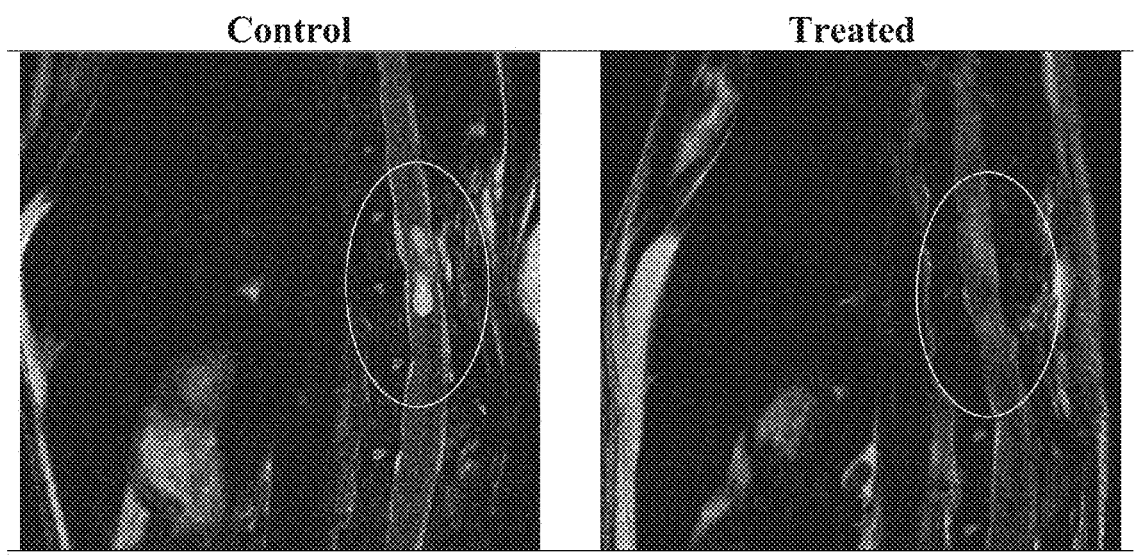
FIG. 4. MRI shows reduced fluid filled cyst (appears bright white in the T2 weighted MR image) formation in rodents treated with a PPy scaffold (shown on right) relative to untreated control (shown at left).
Figure 5:
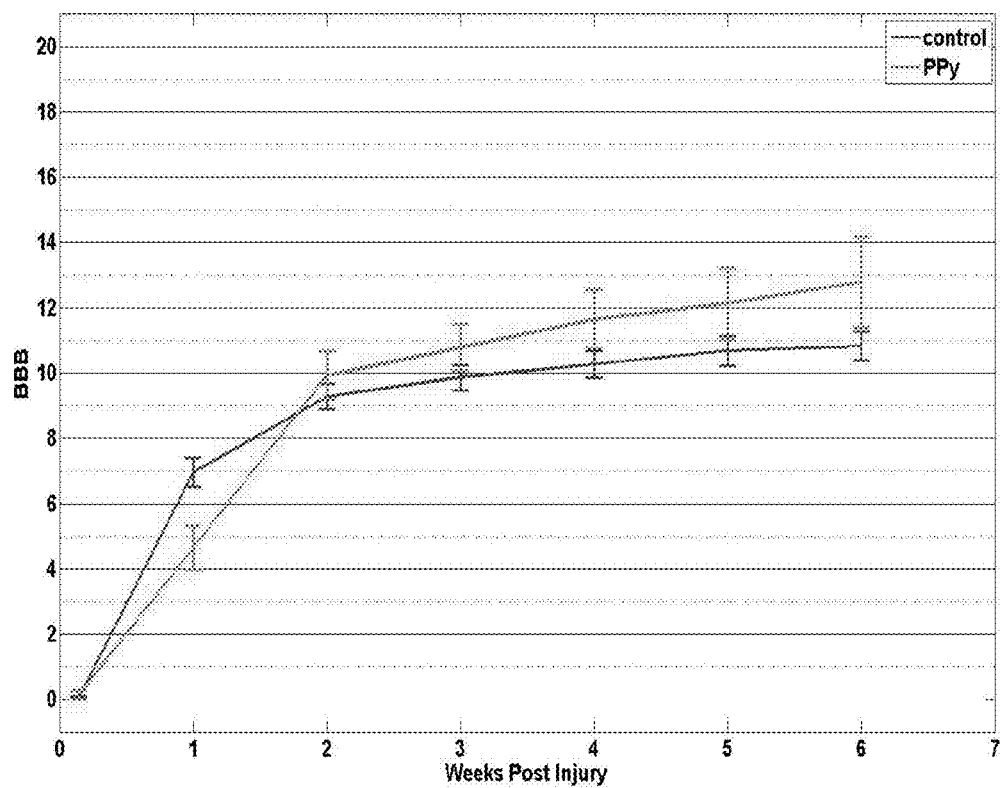
FIG. 5. Open-field locomotor scores for polypyrrole mini-tube-implanted rats (n=8) and lesion-control rats (n=11).

Open-Field Locomotor Scores for Polypyrrole-Implanted Rats and Lesion Control Rats Results from the polypyrrole mini-tube scaffold showed functional locomotor improvement as early as 2 weeks post injury. The amount of functional recovery relative to non-treated controls continues to increase for up to 6 weeks. See FIG. 5. Treated animals are capable of weight-bearing and functional stepping, where non-treated animals show greatly diminished hindlimb function. Magnetic resonance images show that the fluid filled cyst is reduced with a herein described implant. As shown in FIG. 4, the spinal cord is more intact and the cyst is barely visible when treated with polypyrrole. Biodegradable and/or biocompatible polymers are well known in the art and can be used in the present invention.

Example 4

Polypyrrole Mini-Tube Polymer Treated SCIs

Biocompatible polypyrrole polymer mini-tubes demonstrated high affinity to human neuronal stem cells. See FIGS. 3A and 3B, for example. In an in vivo study, a 25 mm contusion injury was delivered via the NYU Impactor on Sprague-Dawley rats. Immediately following injury in the two treatment groups, the cord meninges were incised with a short (approximately 1-3 mm) cut, allowing for neurosurgical decompression and creating a space for insertion of the tube. In scaffold treatment groups, the implants were inserted into the cord, targeting the central canal and surrounding parenchyma. After implantation, the dura was covered and sealed using the Duragen collagen matrix and overlying tissues sutured closed.

Example 5

Fabrication of PPy Mini-Tubes (II)

Tube-like PPy scaffolds were produced by plating the PPy onto a conductive wire mold. This technique can be scaled to produce scaffolds of any length, inner diameter, and outer diameter. Furthermore, surface roughness can be controlled with electroplating temperature (FIG. 2). Scaffold extraction from the template by application of a negative potential in a saline solution. The negative potential causes electrochemical reduction and slightly increases the size of the scaffold. It can then be mechanically dissociated from the platinum wire mold with minimal applied force, resulting in no damage to the material. This technique is an improvement on the prior method of etching the inner wire with harsh organics, making any resulting devices unsuitable for implantation. For in vivo tests in rodents, PPy tube scaffolds were created by electrodeposition of erodible PPy at 100 µA for 40 min onto 250 µm diameter platinum wire. This was followed by reverse plating at 3V for 20 seconds, allowing removal of the scaffold. The resulting tubes of 10-15 mm length were sectioned into 3 mm long pieces for implantation.

Example 6

Cell Maintenance and Seeding on Polymer Mini-Tubes

Murine NSCs (neuronal stem cells) were maintained in serum-containing medium. Scaffolds were soaked in 70% ethanol for 24 hrs, rinsed three times in PBS, and seeded on an orbital shaker with $5\times10^5$ cells/ml at 37° C. in a humidified 5% $CO_2$/air incubator. The medium was changed the next day, and the implants were incubated for 4 more days before implantation.

Example 7

Double Scaffold Fabrication

Both the inner and outer scaffolds were fabricated from a blend of 50:50 poly(lactic-co-glycolic acid) (PLGA) (75%, number average molecular weight, Mn, ~40,000) and a block copolymer of poly(lactic-co-glycolic acid)-polylysine (25%, PLGA block Mn ~30,000, polylysine block Mn ~2000). The PLGA was chosen to achieve a degradation rate of about 30-60 days, and the functionalized polymer was incorporated to provide sites for possible surface modification. The inner scaffold was made using a salt-leaching process: a 5% (wt/vol) solution of the polymer blend in chloroform was cast over salt with a diameter range of 250-500 µm, and the solvent was allowed to evaporate. The salt was then leached in water. The oriented outer scaffold was fabricated using a solid-liquid phase separation technique in the following way: A 5% (wt/vol) solution of the polymers was filtered and injected into silicone tubes which were lowered at a rate of $2.6\times10^4$ m/s into an ethanol/dry ice bath. Once frozen, the dioxane was sublimated using a shelf temperature-controlled freeze drier (VirTis). The scaffolds were then removed, trimmed, assembled, and stored in a vacuum desiccator until use. The resulting product is one wherein the inner scaffold emulates gray matter via a porous polymer layer which can be seeded with stem cells, for example; and the outer scaffold emulates the white matter with long, axially oriented pores for axonal guidance and radial porosity to allow fluid transport while inhibiting ingrowth of scar tissue.

Example 8

Figure 7:
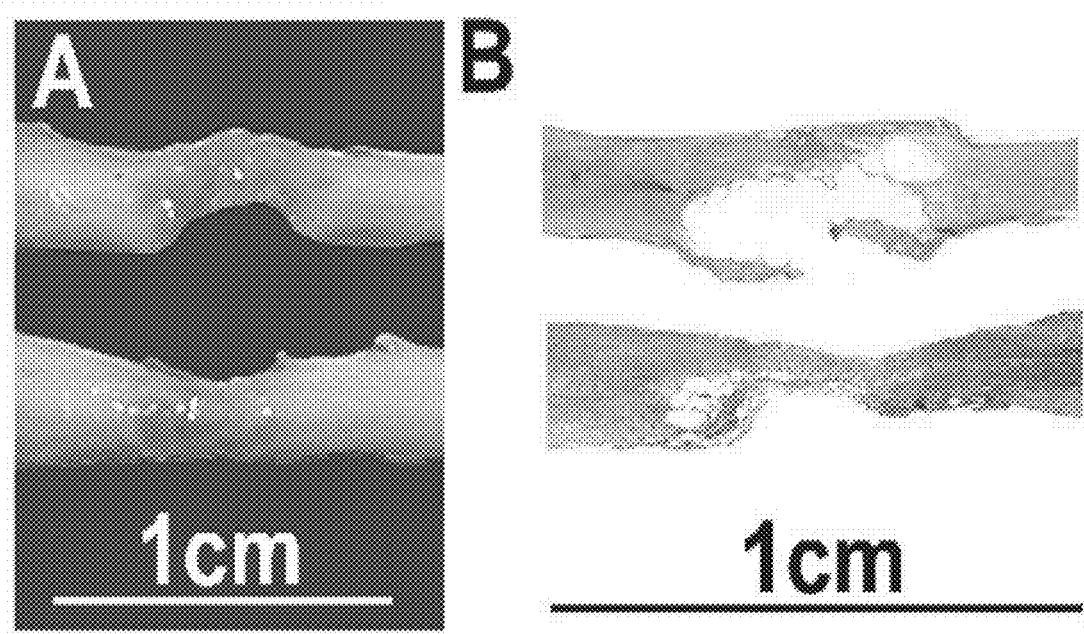
FIG. 7. Spinal cord tissue protection resulting from application of PLGA polymer scaffold into the penetrating lesion site.

Dramatic spinal cord parenchyma protection is observed at both gross pathology (FIG. 7A) and microscopic (FIG. 7B) levels in the penetrating lesion epicenter tissue collected 8 weeks after the lesion (n=8) or the implantation of PLGA polymer patch (n=8). Upper panels of 7A and 7B show the penetrating lesion epicenter morphologies presented in gross pathology (7A upper panel) and microscopic images (7B upper panel). Eight weeks after initial open wound lesion (i.e., T9-T10 segmental removal of half spinal cord from the midline), only little amount of scarring tissue was left to link the spinal cord. In contrast, polymer patched spinal cord (inserted immediately after lesion) demonstrated significant parenchyma protection for the initially intact side of the cord; the spared tissue was clearly discernible at 8 weeks after penetrating lesion insult at levels of both gross pathology (7A lower panel) and microscopic examination (7B lower panel).

Example 9

Open-Field Locomotor Scores for Polypyrrole-Implanted Rats and Lesion Control Rats Results from the polypyrrole scaffold showed functional locomotor improvement as early as 2 weeks post injury. The amount of functional recovery relative to non-treated controls continues to increase for up to 6 weeks. See FIG. 5. Treated animals are capable of weight-bearing and functional stepping, where non-treated animals show greatly diminished hindlimb function. Magnetic resonance images in FIG. 4 show that the fluid filled cyst is reduced with a herein described implant. As shown in the figure, the spinal cord is more intact and the cyst is barely visible when treated with polypyrrole mini-tube scaffold. Biodegradable and/or biocompatible polymers are well known in the art and can be used in the present invention.

Example 10

Figure 6:
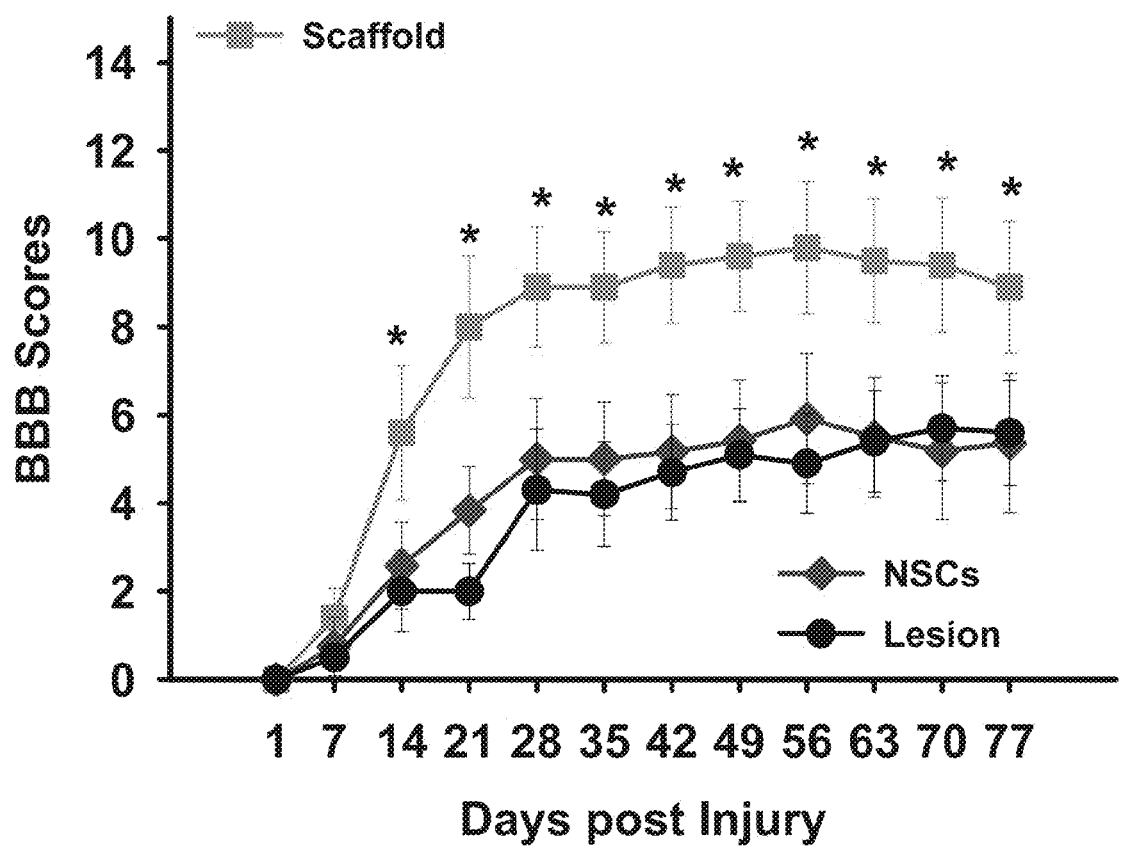
FIG. 6. BBB open-field walking scores for the four groups on the ipsilateral, lesioned side. Hindlimbs were assessed independently to determine the degree of asymmetry. The rate of improvement for the scaffold-treated group was significantly greater than the rate for the stem cells-alone (P<0.001) and lesion-control groups (P<0.004; two-way repeated measures of ANOVA; N=12 each group).

Functional Recovery from Implantation of PLGA Scaffolds Configured to Treat SCIs Basso-Beattie-Bresnahan (BBB) scoring, the standard quantitative metric in the spinal cord injury research field, was used to evaluate open-field locomotion at one day postsurgery and at weekly time points over the course of 6 weeks post-injury. Results from the PLGA double-scaffold configured to treat SCI showed functional locomotor improvement as early as 2 weeks post injury. See FIG. 6. The amount of functional recovery relative to non-treated controls continued to increase for up to 8-10 weeks. The study was ended at the end of week 8 or 10. In additional studies, rodents were kept for over one year and demonstrated sustainable functional recovery as well as no pathology in reaction to the product. Because the average lifespan of a rat is 2 years, the "one year plus" study demonstrates effectiveness of the herein described scaffolds.

Example 11

BBB Open-Field Walking Scores

BBB open-field walking scores for the four groups on the ipsilateral, lesioned side. See FIG. 9. Hindlimbs were assessed independently to determine the degree of asymmetry. The rate of improvement for the scaffold plus cells group was significantly greater than the rate for the cells-alone (P<0.001) and lesion-control groups (P<0.004; two-way repeated measures of ANOVA). Additionally, the scaffold alone treated group showed significant improvement in open-field locomotion compared with the lesion-control group (P<0.05) (P<0.05) for all time points from 14 days after SCI on, and the cells-alone group (P<0.05) at 21, 35 and 42 days post injury (ANOVA, Bonferroni post hoc analysis).

Example 12

Cell Maintenance and Seeding

Murine and human NSCs (neuronal stem cells) were maintained in serum-containing medium. Saffoleds were soaked in 70% ethanol for 24 hrs, rinsed three times in PBS, and seeded on an orbital shaker with $5 \times 10^5$ cells/ml at 37° C. in a humidified 5% $CO_2$/air incubator. The medium was changed the next day, and the implants were incubated for 4 more days before implantation.

Example 13

Histopathology

Conventional histopathologic analysis was performed on the spinal cord tissue to determine changes of lesion scale, secondary injury events and healing processes. Microscopic images proved that the injury area was significantly reduced with our implant treatment. The spinal cord also demonstrated mitigated scarring as indicated by the reduced astrogliosis, a pathology which was impeded by both polymer plus stem cells and by polymer alone as well, is more intact and the cyst is barely visible when treated with polypyrrole.

Example 14

Figure 9:
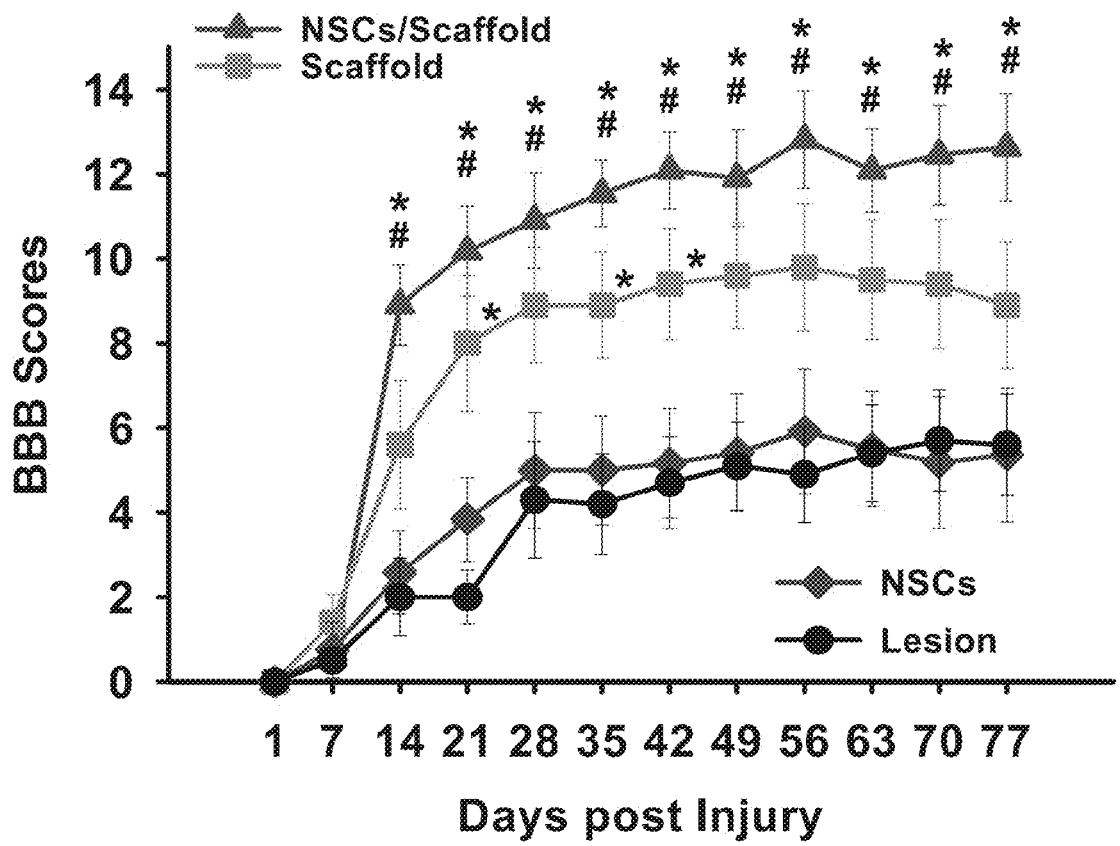
FIG. 9. Functional recovery in rats with penetrating injury to the T9-10 spinal cord after double-scaffold PLGA implant treatment.

The level of functional recovery after the same model of injury is further lifted by treatment of human NSCs seeded PLGA polymer as demonstrated in FIG. 9. 100% of treated animals were capable of weight-bearing and functional stepping. As shown in the figure (FIG. 9), 50% of treated animals met the rigorous criteria of Consistent plantar stepping and Consistent FL-HL coordination during gait; and Toe clearance occurs frequently during forward limb advancement; Predominant paw position is parallel at initial contact and rotated at lift off, corresponding to a BBB score of 16 or higher. None of the non-treated control animals reached this high standard of recovery, but rather exhibited greatly diminished hind limb function.

Example 15

Single Scaffold Fabrication

The single scaffold was fabricated from a blend of 50:50 poly(lactic-co-glycolic acid) (PLGA) (75%, number average molecular weight, Mn, ~40,000) and a block copolymer of poly(lactic-co-glycolic acid)-polylysine (25%, PLGA block Mn ~30,000, polylysine block Mn ~2000). The PLGA was chosen to achieve a degradation rate of about 30-60 days, and the functionalized polymer was incorporated to provide sites for possible surface modification. The single scaffold was made using a salt-leaching process: a 5% (wt/vol) solution of the polymer blend in chloroform was cast over salt with a diameter range of 250-500 µm, and the solvent was allowed to evaporate. The salt was then leached in water. The product is a single porous polymer layer which can be seeded with stem cells, for example.

Example 16

Spinal Cord Tissue Analysis

Pathology, histology, and immunocytochemistry analysis of spinal cord tissue (via GFAP and DAPI staining of glial cells at 2 mm rostral to the lesion epicenter) revealed that PLGA scaffold alone and especially PLGA scaffold seeded with human neural stem cells markedly reduced scarring formation in the injured area. Wright's staining of infiltrated polymorphonucleic leukocytes (PNLs) in spinal cord tissues 2 mm rostral to the lesion epicenter show that PLGA scaffold alone and especially PLGA scaffold seeded with human neural stem cells markedly impeded infiltration of PNLs, a major iNOs (inducible nitric oxide synthase) carrier, into the spinal cord.

Example 17

Spinal Cord Injury (SCI) Surgical Procedures and Animal Care

Surgical Procedures and Animal Care. Fifty adult female Sprague-Dawley rats were used. Animals were anesthetized with a 4% chloral hydrate solution (360 mg/kg i.p.). Using a dissecting microscope, a laminectomy was made at the 9th-to-10th thoracic (T9-T10) spinal vertebrae, followed by a lateral hemi-section at the T9-T10 level by creating a 4-mm-long longitudinal cut along the midline of the cord with a No. 11 surgical blade, followed by lateral cuts at the rostral and caudal ends and removal of the tissue by aspiration. The surgical blade was repeatedly scraped along the ventral surface of the vertebral canal, followed by aspiration to remove any residual fibers at the lesion site. After gelfoam-triggered hemostasis occurred, an independent blinded observer confirmed the adequacy of the length and breadth of the lesion. Only at that time was the surgeon informed of the treatment (previously prepared) to be administered to the lesion. The lesion was affirmed a priori to be similar across all experimental groups and animals. Either the full treatment, consisting of insertion of the NSC seeded scaffold ("scaffold plus cells," n=13), or one of three control treatments was performed: (a) polymer implant without NSCs ("scaffold alone," n=11; (b) NSCs suspended in medium ("cells alone," n=12); or (c) hemi-section alone ("lesion control," n=12). Surgeries were performed in a randomized block design. The surgeries for the implant plus controls were performed on the same day to minimize differences between groups arising from any refinement in surgical technique during the study, and the order was varied each day to reduce surgical bias. Hemi-sections were alternated between the right and left sides to further reduce bias. Following either the full or control treatment, the musculature was sutured, skin closed, and the animal recovered in a clean cage on a heating pad. Ringer's lactate solution (10 ml) was given daily for 7 days post-op and bladders were evacuated twice daily until reflex bladder function was established.

Because immunosuppressive agents such as cyclosporin A have been shown to be neuroprotective on their own, these experiments were performed without such neuroimmunophilins to avoid this confounding variable. Donor cells were nevertheless present at the end of the study. A separate group of scaffold plus cells animals underwent the same procedures as above and were maintained for one year.

All procedures were reviewed and approved by the Animal Care and Use Committee of our institutions.

Example 18

Functional Recovery Analysis Summary for Bandage-Scaffold

Figure 8:
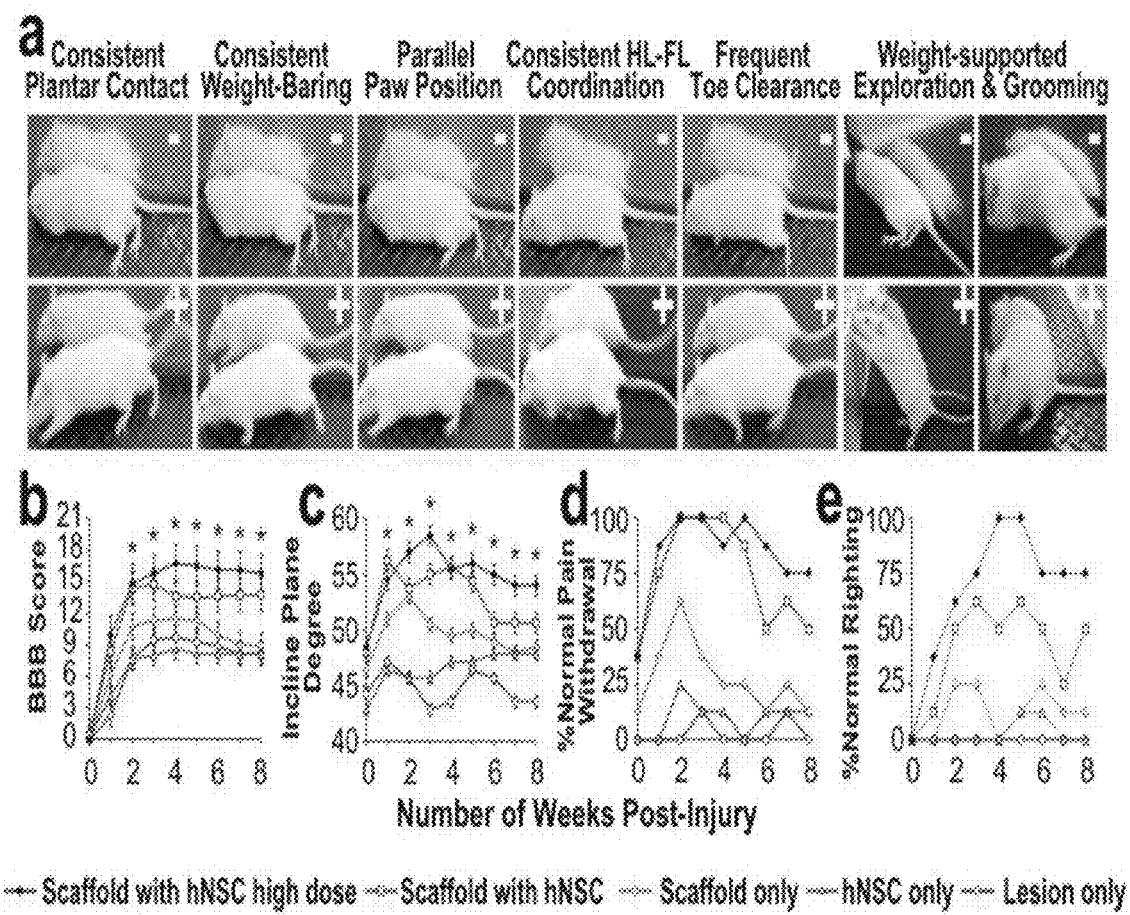
FIG. 8. Functional recovery analysis summary for bandage-scaffold. a, Montages of still images of animal open-field walking in "lesion only" (top row) and "scaffold with high dose hNSCs" (bottom row). b, Lesion side BBB open-field walking scores. The absolute scores of groups treated with hNSCs seeded in single-scaffolds (i.e., 16-17 in average) are significantly higher than "hNSCs only" group (BBB score of 9 in average; P=0.004 for regular dose, P<0.001 for high dose), "scaffold only" group (P=0.004 for regular dose, P=0.001 for high dose; the scaffold alone group received PLGA polymer in a single porous layer design, and "lesion only" group (P<0.001 for regular dose, P=0.001 for high dose, ANOVA, Bonferroni post hoc analysis). The rate of improvement also shows a significantly greater value in hNSC seeded in scaffold groups than the "hNSCs only" group (P=0.004 for regular dose, P<0.001 for high dose, two-way repeated measures of ANOVA), scaffold group (P=0.004 for regular dose, P<0.001 for high dose), and "lesion only" group (P=0.004 for regular dose, P<0.001 for high dose). c, Inclined plane tests. When facing downward, the hNSC+scaffold treated rats could stabilize their bodies on inclined boards angled at significantly higher degrees (Kruskal-Wallis test, P<0.001). Parametric and non-parametric analysis both reveal similar results. d, Pain withdrawal reflex scores. The left curve panel is the percentage of animals in each group scoring 2, corresponding to normal response. The right panel is the percentage of animals in each group scoring 3, indicating hyperactive response. The two panels consistently indicate that the groups receiving hNSCs seeded in single-scaffolds showed significantly improved hind limb reflex which was correlated with hNSC doses (Pearson $\chi^2$ test of independence). e, Percentage of animals in each group demonstrating normal righting reflex. Groups receiving hNSCs seeded in single-scaffolds had significantly higher percentage of rats that recovered their righting reflex comparing to other groups (Pearson $\chi^2$ test).

See FIG. 8, wherein a, Montages of still images of animal open-field walking in "lesion only" (top row) and "scaffold with high dose hNSCs" (bottom row). b, Lesion side BBB open-field walking scores. The absolute scores of groups treated with hNSCs seeded in single-scaffolds (i.e., 16-17 in average) are significantly higher than "hNSCs only" group (BBB score of 9 in average; P=0.004 for regular dose, P<0.001 for high dose), "scaffold only" group (P=0.004 for regular dose, P=0.001 for high dose, and "lesion only" group (P<0.001 for regular dose, P=0.001 for high dose, ANOVA, Bonferroni post hoc analysis). The scaffold alone group received PLGA polymer in a single porous layer design. The rate of improvement also shows a significantly greater value in hNSC seeded in scaffold groups than the "hNSCs only" group (P=0.004 for regular dose, P<0.001 for high dose, two-way repeated measures of ANOVA), scaffold group (P=0.004 for regular dose, P<0.001 for high dose), and "lesion only" group (P=0.004 for regular dose, P<0.001 for high dose). c, Inclined plane tests. When facing downward, the hNSC+scaffold treated rats could stabilize their bodies on inclined boards angled at significantly higher degrees (Kruskal-Wallis test, P<0.001). Parametric and non-parametric analysis both reveal similar results. d, Pain withdrawal reflex scores. The left curve panel is the percentage of animals in each group scoring 2, corresponding to normal response. The right panel is the percentage of animals in each group scoring 3, indicating hyperactive response. The two panels consistently indicate that the groups receiving hNSCs seeded in single-scaffolds showed significantly improved hind limb reflex which was correlated with hNSC doses (Pearson $\chi^2$ test of independence). e, Percentage of animals in each group demonstrating normal righting reflex. Groups receiving hNSCs seeded in single-scaffolds had significantly higher percentage of rats that recovered their righting reflex comparing to other groups (Pearson $\chi^2$ test).

Although the particular aspects of the invention have been described, it would be obvious to one skilled in the art that various other modifications can be made without departing from the spirit and scope of the invention. It is therefore intended that all such changes and modifications are within the scope of the appended claims.

We claim:
1. A biodegradable and/or bioabsorbable polymeric article suitable for insertion within the epicenter of a lesion at the site of a spinal cord compression injury in a human, wherein the article comprises a a single layer linear aliphatic polyester scaffold having a degradation rate of about 30 to about 60 days.

2. The polymeric article of claim 1, wherein the linear aliphatic polyester is a polyglycolide or a co-polymer of poly(glycolide-co-lactide).

3. The polymeric tubular article of claim 1, comprising poly(lactic-co-glycolic acid).

4. The polymeric article of claim 1, comprising poly(lactic-co-glycolic acid) and a functionalized polymer providing sites for surface modification.

5. The polymeric article of claim 3, wherein the poly(lactic-co-glycolic acid) has an average molecular weight of Mn ~40,000.

6. The polymeric article of claim 1, wherein the article has an overall diameter of between about 0.1 microns and 10 millimeters.

7. The polymeric article of claim 6, wherein the article has an overall diameter of between about 50 and 175 microns.

8. The polymeric article of claim 1, wherein the article comprises a monomer selected from the group consisting of a glycolide, lactide, dioxanone, caprolactone, trimethylene carbonate, ethylene glycol and lysine.

9. The polymeric article of claim 1, wherein the article is smaller than the length of the lesioned area of the spinal cord compression injury.

10. The polymeric article of claim 1, wherein the article is longer than the length of the lesioned area of the spinal cord compression injury.

11. The polymeric article of claim 10, wherein the article is approximately 1.5 times longer than the length of the lesioned area of the spinal cord compression injury.

12. The polymeric article of claim 10, wherein the article is about 1.2 to about 3 times longer than the length of the lesioned area of the spinal cord compression injury.

13. The polymeric article of claim 1, further comprising one or more medicinal agents.

14. The polymeric article of claim 13, wherein the one or more medicinal agents are selected from the group consisting of anti-inflammatory agents, growth factors and stem cells.

15. The polymeric article of claim 14, wherein the stem cells are selected from the group consisting of neuronal stem cells and mesenchymal stem cells.

16. The polymeric article of claim 15, wherein the neuronal stem cells are human neuronal stem cells.

17. The polymeric article of claim 1, further comprising pharmaceutically or biologically active substances.

18. The polymeric article of claim 17, wherein the biologically active substance is a biological tissue.

* * * * *

UNITED STATES PATENT AND TRADEMARK OFFICE
CERTIFICATE OF CORRECTION

| | | |
|---|---|---|
| PATENT NO. | : 9,101,695 B2 | Page 1 of 1 |
| APPLICATION NO. | : 14/496742 | |
| DATED | : August 11, 2015 | |
| INVENTOR(S) | : Langer et al. | |

It is certified that error appears in the above-identified patent and that said Letters Patent is hereby corrected as shown below:

In the claims

Column 18, Line 65, Claim 1, delete "a a" and insert -- a --, therefor.

Column 19, Line 4, Claim 3, delete "polymeric tubular" and insert -- polymeric --, therefor.

Signed and Sealed this
Twenty-second Day of December, 2015

Michelle K. Lee
*Director of the United States Patent and Trademark Office*